(12) United States Patent
Schwitzer (10) Patent No.: US 9,352,072 B2
(45) Date of Patent: May 31, 2016

(54) MATERIAL COMPOSITION HAVING REDUCED FRICTION COEFFICIENT USED FOR MEDICAL TUBES

(71) Applicant: BIOTRONIK AG, Buelach (CH)

(72) Inventor: Alwin Schwitzer, Buelach (CH)

(73) Assignee: Biotronik AG, Buelach (CH)

( * ) Notice: Subject to any disclaimer, the term of this patent is extended or adjusted under 35 U.S.C. 154(b) by 0 days.

(21) Appl. No.: 14/404,216

(22) PCT Filed: May 16, 2013

(86) PCT No.: PCT/EP2013/060183
§ 371 (c)(1),
(2) Date: Nov. 26, 2014

(87) PCT Pub. No.: WO2013/189672
PCT Pub. Date: Dec. 27, 2013

(65) Prior Publication Data
US 2015/0112026 A1    Apr. 23, 2015

Related U.S. Application Data

(60) Provisional application No. 61/661,812, filed on Jun. 20, 2012.

(51) Int. Cl.
| | |
|---|---|
| *C08L 29/00* | (2006.01) |
| *A61L 29/04* | (2006.01) |
| *A61L 29/08* | (2006.01) |
| *A61L 29/14* | (2006.01) |
| *C08L 23/06* | (2006.01) |

(52) U.S. Cl.
CPC ............ *A61L 29/049* (2013.01); *A61L 29/041* (2013.01); *A61L 29/085* (2013.01); *A61L 29/14* (2013.01); *C08L 23/06* (2013.01); *A61L 2400/10* (2013.01); *A61L 2420/02* (2013.01); *A61L 2420/06* (2013.01)

(58) Field of Classification Search
CPC ..... A61L 29/085; A61L 29/14; A61L 29/049; A61L 29/041; A61L 2400/00; A61L 2420/02; A61L 2420/06; C08L 23/06; C08L 23/0823
See application file for complete search history.

(56) References Cited

U.S. PATENT DOCUMENTS

| | | | | |
|---|---|---|---|---|
| 7,267,856 | B2 * | 9/2007 | Patel et al. | B29C 65/08 383/122 |
| 7,803,305 | B2 * | 9/2010 | Ahern et al. | A61B 5/1438 264/255 |
| 2006/0093831 | A1 | 5/2006 | Jester | |

FOREIGN PATENT DOCUMENTS

EP    2186634    5/2010

OTHER PUBLICATIONS

Constant, David R. "Cyclic-olefinic copolymers as non-migrating, polymeric slip additives in." Place Conference, Sep. 12, 2002, Boston, MA Expanded Summary from the World Wide Webhttp://pffc-online.com/ar/96-paper-cyclicolefinic-copolymers-nonmigrating. Dated Jul. 1, 2003.*
PCT/EP2013/060183 International Search Report mailed Oct. 2, 2013.
Constant, David R. "Cyclic-olefinic copolymers as non-migrating, polymeric slip additives in." Place Conference, Sep. 12, 2002, Boston, MA US, Database CA [Online} Chemical Abstracts Service, XP002712375, Database Accession No. 2003:100673.
Kolarik et al. "High-density Polyethylene/cycloolefin copolymer blends, Part 1: Phase structure, dynamic mechanical, tensile, and impact properties." Polymeric Engineering and Science, 2005, pp. 817-826; XP002712371 Abstract.
Kolarik et al. "High-density polyethylene/cycloolefin copolymer blends, Part 2: non linear tensile creep." Polymer Engineering and Science, 2006, pp. 1363-1373, XP002712372 Abstract.
Pimbert, Sylvie. Evaluation of the fractionated crystallization of isotatic polypropylene and high density polyethylenes in their blends with cycloolefin copolymers.: Macromol. Symp., 2003, 203:277-283, XP002712370 p. 280, p. 282.

* cited by examiner

*Primary Examiner* — Nathan M Nutter
(74) *Attorney, Agent, or Firm* — Wagenknecht IP Law Group PC (57) ABSTRACT

Mixtures made of PE and COC, in particular for use in medical materials, so as to reduce the frictional forces. The mixtures comprising or consisting of PE and COC, wherein ≥70% by weight, preferably ≥90% by weight, and still more preferably 100% by weight, relative to the total mass of PE, of PE in the mixture is HDPE.

11 Claims, 7 Drawing Sheets

MATERIAL COMPOSITION HAVING REDUCED FRICTION COEFFICIENT USED FOR MEDICAL TUBES

CROSS REFERENCE TO RELATED APPLICATIONS

This is a Section 371 US national phase entry of PCT/EP2013/060183, filed May 16, 2013, which claims benefit of priority to U.S. provisional patent application Ser. No. 61/661,812 filed Jun. 20, 2012; the contents of each are herein incorporated by reference in their entirety.

TECHNICAL FIELD

The invention relates to a mixture comprising or consisting of polyethylene (PE) and cyclic olefin copolymer (COC), wherein a content of ≥70% by weight relative to the total mass of PE in the mixture is high-density polyethylene (HDPE). The invention further relates to solid bodies, consisting of or comprising such a mixture, and to solid bodies which are medical products, comprising a mixture of PE and COC.

The invention further relates to the use of a mixture made of PE and COC to reduce the friction of an object, in particular with respect to metal, to a method for producing a medical object, comprising the step of jointly extruding a corresponding mixture made of PE and COC, and to a method for reducing the friction of an object, in particular with respect to metal, comprising the step of at least partially coating the object in the region in which the friction with metal can occur, comprising a mixture made of PE and COC.

BACKGROUND

There is a constant need for improved materials for medical applications, and particularly in the field of medical tubes and catheter guide devices. An important aspect are the intrinsic frictional properties, for example with respect to metal, for applications in which a wire is to be advanced in a corresponding tube system or, in general terms, for areas in which contact may occur between a surface and metal as part of the medical applications.

In the prior art, high-density polyethylene (HDPE) or polytetrafluoroethylene (PTFE) is used, for example in tubes for medical applications, so as improve the frictional properties. These materials are used in particular as the inner layer of multi-layer materials. Guide catheters having a PTFE inner layer, or tubes made of HDPE, are thus known, for example, from the prior art as protectors for catheters.

As an alternative, the surfaces of tubes are coated in order to reduce the intrinsic material properties, so as to deliberately control the properties hydrophilically or hydrophobically.

A combination comprising a cyclic olefin copolymer (COC) and a catheter is known from WO 2005/044314 A2, for example.

KR 100429660 B1 discloses combinations comprising polyethylene, and more specifically mixtures made of low-density polyethylene (LDPE) and high-density polyethylene (HDPE), and cyclic olefin copolymer as film material, having properties, for example chemical resistance, scratch resistance and flexibility, equal to PVC films, as replacement material for softened PVC (softened PVC films).

The drawback of the existing known solutions is that the intrinsic frictional properties of polymers that are presently used for medical tubing is just barely sufficient, for example for the guide wire friction of inside shafts in RX catheters. So as to prevent excessive force application when inserting the catheter on the guide wire and possible injury to the vascular walls, cardiologists desire catheters that have the lowest possible frictional forces.

SUMMARY OF THE INVENTION

The added coating of catheter surfaces, for example, with hydrophobic or hydrophilic coating agents is associated with the risk that these coatings, and specifically hydrophilic coatings, which interact with biological liquids (blood), may release substances such as those which are defined in ISO 10093-17 (2002) §3.10 and which require complex determination and classification.

Against this background, it was the object of the present invention to provide a novel material which is able to provide a surface having improved frictional behavior, in particular with respect to metal, especially for medical applications. Moreover, it was desirable for the corresponding material to have a property window which allows use of the same in a variety of medical applications. In addition to biological compatibility, the properties that shall be mentioned here also include properties such as flexibility, trackability, conduct under tensile and/or compressive stress, and/or usability in a variety of production methods and/or cost effectiveness in production.

This object is achieved by a mixture comprising or consisting of PE and COC, wherein ≥70% by weight, preferably ≥90% by weight, and still more preferably 100% by weight, relative to the total mass of PE, of the PE in the mixture is HDPE, and the COC content in the PE/COC mixture preferably ranges between 5 and 25% by weight, relative to the total mass of PE and COC.

For this purpose, COC denotes cyclic olefin copolymer, PE denotes polyethylene, and HDPE denotes high-density polyethylene.

Within the meaning of the present application, HDPE is a special fraction of PE, wherein HDPE within the meaning of the present application is a PE that has a density of ≥0.934 $g/cm^3$, which is higher than that of LDPE (0.915-0.933). Moreover, the crystallinity of HDPE is usually higher than that of LDPE, which manifests itself, for example, in the higher melting temperature (HDPE: ~130° C., LDPE: ~110° C.). The higher density of HDPE as compared to LDPE is achieved by a considerably lower "degree of long-chain branching".

PE, notably in the form of HDPE, is generally present in semi-crystalline form, which is preferred for the invention. In contrast, COC is present in amorphous form.

To the extent that the mixture according to the invention is a mixture of granules of the two polymer types, this mixture shall be considered to be a preliminary product of the proper mixture according to the invention. Using a suitable melting and mixing method, a copolymer can be produced from this mixture of granules, the copolymer having a considerably lower friction force than semi-crystalline HDPE, especially with respect to a metallic friction partner. Comparison experiments showed a reduction in the friction forces of approximately 30%. It was not predictable from the prior art that this effect was achievable by a corresponding copolymer and it is thus surprising.

Particularly good effects within the meaning of the aforementioned desired properties of the invention, and especially with respect to the decrease in friction forces with respect to (metallic) friction partners, can be achieved when the weight percentage relationships between the total mass of PE and the total mass of COC in the mixture according to the invention are 60-98% by weight to 40-2% by weight, and preferably 75-90% by weight to 25-5% by weight, based on the total mass of PE and COC in the mixture. The aforementioned weight percentage relationship still more preferably is 80-95% by weight to 20-5% by weight.

A possible explanation for the resulting advantages—without being bound to a theory—may be that polyethylene, and more particularly HDPE and COC, are only miscible to some extent (see Ticona/Celanese David R. Constant, ANTEC Exchange 2002). During the extrusion process, the melt leaves the shaping section at a temperature of 225° C. (see Example 1) and the extrudate is cooled in water. The amorphous domains of the melt consisting of the amorphous COC, having a glass transition temperature (Tg) of 138° C. for example (see Example 1), solidify before the semi-crystalline domains, which consist of HDPE, can crystallize because HDPE crystallizes at a temperature of less than 125° C. (in the case of HDPE of Example 1 at 118° C., see Borealis: Bormed presentation 2005, page 29). A structure in the melt of the HDPE is forced upon the mixture due to the solidification of the amorphous COC components. The HDPE, which is still in the molten state, crystallizes in this COC structure. Because semi-crystalline polymers, and thus also semi-crystalline HDPE, shrink during crystallization, which is to say the density to the volume decreases (see Borealis: Bormed presentation 2005, page 67 PVD diagram), HDPE crystallizes in the structure made of solidified COC and, after the mixture according to the invention cools, the melt turns into an extrudate surface having a surface roughness of ~2 µm, for example. For this effect, it is thus preferred that the glass transition temperature (Tg) of the (amorphous) COC is higher than the crystallization temperature of the (semi-crystalline) HDPE. It is further advantageous for the temperature of the molten mixture not to be too high (such as no more than 100° C. above the glass transition temperature Tg of the COC).

Compared to an identical tube made of pure HDPE, a tube made of the material composition according to the invention (containing 10% COC and 90% HDPE) exhibits a reduction of the dynamic friction coefficient (CoF) by 0 to 40%, preferably 10 to 35%, and still more preferably by 20 to 35% (see Example 1).

Further preferred is a mixture according to the invention, wherein the PE has a melting temperature of 124° C. to 135° C. and/or a density of 0.934 g/ml to 0.966 g/ml and/or a melt flow index (MFI) of 0.3 g/10 min to 5 g/10 min, and the COC has a glass transition temperature (Tg) of 130° C. to 160° C. and/or a melt volume rate (MVR) of 10 ml/10 min to 20 ml/10 min and/or a refractive index of 1.52 to 1.54.

It is particularly preferred in this connection that the PE is selected from extrudable PE, preferably from the group of high-density polyethylene (HDPE), for example Petrothene® LM 6007-00, Purel® GD 6250 or Bormed® HE2581-PH, and the preferred amorphous COC is selected from high-Tg COC types (for example the TOPAS® products).

The desired properties windows can be achieved particularly well when using the aforementioned preferred and particularly preferred materials.

The invention further relates to a solid body, preferably to an extrusion product, for example a profiled, tube or film extrudate, an extrusion blow-molded product, an injection-molded product, or an injection blow-molded product consisting of a mixture according to the invention.

Within the meaning of the present application, in a solid body, mixing of the two polymers has occurred at least partially, and preferably fully, in the liquid state. It is preferred according to the invention for the mixing to be homogenous.

In a solid body according to the invention, the advantages of the material combination, and more particularly the reduced friction with respect to metal, can be utilized particularly well.

A solid body according to the invention is preferred to this end, wherein the mixture according to the invention consists of PE and COC.

It shall be noted here that a solid body within the meaning of this text can also be a part of a (larger) solid body. Similarly, a solid body within the meaning of the present invention is a region of a larger solid body, or of a larger assembly, which can be clearly distinguished from other regions in terms of the material composition thereof, and more particularly it refers to the situation that a multi-layer system exists, in which one of the layers is a solid body according to the invention.

The invention also relates to a solid body comprising or consisting of a mixture made of PE and COC and/or comprising or consisting of a solid body according to the invention described above, wherein the solid body is selected from the group consisting of a medical tube, in particular a single-layer tube or multi-layer tube, and notably selected from the group consisting of balloon tube, a charging tube for a delivery system, outside shaft for an RX or over-the-wire catheter, and inner layer or outer layer of coextruded multi-layer tubes, and inside shaft of a catheter, outside shaft of a catheter, protector for a catheter, and catheter, in particular a guide catheter, insertion system for electrodes, release tubes for (nitinol) stents or (nitinol) heart valve stents.

To this end, it also applies to the mixture made of PE and COC not comprising the aforementioned contents of HDPE that the other features and feature combinations described above as being preferred are likewise preferred.

The solid bodies according to the invention, and more particularly the preferred solid bodies, have a number of advantages:

They are relatively easy to produce using generally available methods, for example by means of tube extrusion in the case of tubes.

The materials are accessible and acceptable in terms of price.

The solid bodies exhibit low friction with respect to metal, which is particularly desirable especially in applications in which advancement by means of a wire is required in a volume of a tube. Conceivable applications include, for example, the stent application, balloon dilatation catheters, guide catheters, and catheters for probes.

An additional hydrophilic or hydrophobic coating so as to improve the frictional behavior is not required.

The solid bodies according to the invention are biocompatible, but can in general also be employed in areas other than those close to the body.

If the material thickness is suitably selected, the solid bodies are sufficiently flexible.

As already mentioned above, it shall be pointed out again that a particular advantage is the low trackability of the solid bodies according to the invention. Trackability shall be understood to mean the following: Trackability is the ability of a catheter or stent system to pass through the vascular system and be placed at the stenosis (constricted site). It is defined by the proximal force that is required to push the catheter forward through a vessel section.

Trackability is preferably measured according to the following method: Trackability is measured using a model (according to K.-P. Schmitz et al; "Biomol. Technik" 48 (2003) Supplement pp. 66-67) which simulates the anatomic geometry of vessels. To this end, a guide wire is pushed through the model. The catheter is introduced in the model on the guide wire. The catheter is then advanced on the guide wire in the model and the force necessary to do so is measured proximally.

In accordance with what was described above, it is preferred for a solid body according to the invention to be part of a stent application device or of a balloon dilatation catheter. In accordance with what was described above, the invention further relates to the use of a mixture made of PE and COC, as defined above, to reduce the friction of an object with respect to metal.

The use according to the invention can take place in particular by coating corresponding surfaces. The coating can, of course, also be used to reduce the friction with respect to materials other than metal.

To this end, it is obvious to a person skilled in the art that only those surfaces will be coated with the mixture according to the invention which will lead to a decrease in friction with respect to the friction partner, preferably with respect to metal. A reduction in friction within the meaning of the present application exists when a trackability test, as described above, shows a lower value for a surface coated with the mixture according to the invention than for the surface not containing this coating.

The invention further relates to a method for producing a medical object, comprising the following step:
  jointly extruding a mixture of PE and COC, as defined above.

Extrusion is a particularly suitable option for producing a plurality of articles (solid bodies), notably medical articles.

The invention further relates to a method for reducing the friction of an object with respect to metal, comprising the following step:
  coating the object at least partially in the region in which the friction with metal can occur, using a mixture of PE and COC as defined above.

The invention will be described in more detail hereafter based on examples and figures.

The examples below are intended to highlight the advantages of the material composition according to the invention on a complicated system, without thereby limiting the use in other medical products, notably tube, that require reduced friction.

Definitions:

The terms "trackability" and "pushability" that are used are known to a person skilled in the art and are defined in ISO 25539-2:2008, sections 8.5.1.12 and 8.5.1.9.

DESCRIPTION OF THE DRAWINGS

Legends for FIGS. 1 to 5 (see also below)

DETAILED DESCRIPTION

EXAMPLE 1

Extrusion of a 3-layer Inside Shaft

A 3-layer inside shaft, consisting of a polyamide-based outer layer, an adhesion promoter intermediate layer, and an inner layer, was coextruded with the mixture according to the invention by melting
  the polyamide-based outer layer, consisting of polyamide 12 (Grilamid L25 from EMS-CHEMIE) in a first extruder,
  the adhesion-promoting intermediate layer, consisting of a maleic acid anhydride-grafted LDPE (specifically Admer® NF 408-E, from Mitsui), in a second extruder, and
  the material composition according to the invention, consisting of 90% wt/wt granules of a semi-crystalline HDPE (Bormed® HE2581-PH from Borealis) and 10% wt/wt of the amorphous cyclic olefin copolymer (COC, specifically TOPAS® 6013 from TOPAS) in a third extruder.

The separate melts were delivered to a tube shaping section and the individual polymer melts are arranged such that the melt of the first extruder forms the outer layer, the melt of the second extruder forms the adhesion-promoting intermediate layer, and the melt of the third extruder forms the inner layer of the coextruded tube. The inner layer thus created forms a lumen of the coextruded tube.

Customary temperatures were used from the melting processes in the separate extruders. For the first extruder, rising temperatures from 230° C. to 250° C. were used, for the second extruder rising temperatures from 210° C. to 225° C. were used, and for the third extruder rising temperatures from 210° C. to 225° C. were used.

The coextruded tubes have the following dimensions:

Outside diameter: 0.56±0.02 mm, inside diameter: 0.42±0.01 mm, single wall thickness: 0.07 mm with a layer thickness distribution of the 3 coextruded tubes of 60% to 80% of the outer layer made of PA12, and together 20% to 40% of the intermediate layer and the inner layer according to the invention.

The coextruded tube thus produced exhibits the following mechanical properties.
tensile strength: 13.5 N±1.0 N
elongation at break: 375%±25%
stretching force: 3.0 N±0.4 N
elongation at yield: 5.0%±0.2%

Compared to a reference tube, the inner layer of which consists of a semi-crystalline HDPE (Bormed® HE2581-PH or Purell® GD6250 or Petrothene® LM 6007-00) instead of the material composition according to the invention, the tubes thus produced exhibit considerably lower friction with respect to a guide wire (for example Galeo M 014), which is used for vascular interventions.

Determining the Friction Coefficient (CoF)

The CoF was determined by means of a rope friction test according to the "Euler Eytelwein formula", in which the tube to be tested (for example an inner tube having the dimensions listed above from Example 1) was fixed to a stationary roll having a radius of 32 mm and an angle of wrap of 180° C. The tube thus fixed was placed in a track bath from MSI in distilled water at 37±2° C. The length of the curvature in this case is 50.3 mm. A guide wire (Galeo M "014) was guided through the lumen of the tube thus fixed. A constant load of 0.5 N was applied to the wire at the proximal end of the guide wire. The distal end was moved at a speed of 450 mm/min 100 mm in one direction and 100 mm in the other direction and the resulting force was measured. Based on the resulting force and the applied constant force of 0.5 N, the friction coefficient (CoF) was calculated according to $F_{resultiernd} = F_{konst} \cdot CoF$.

A CoF of 0.23 was determined for a tube consisting of the material composition according to the invention from Example 1, and a CoF of 0.28 was determined for a reference tube having the same dimensions and comprising an inner layer made of pure HDPE (Purell GD6250). The friction coefficient CoF thus determined for the reference tube is 0.28 to 0.33, in agreement with values from the literature (Polymer Data Handbook) for friction coefficients of HDPE.

Figure 1:
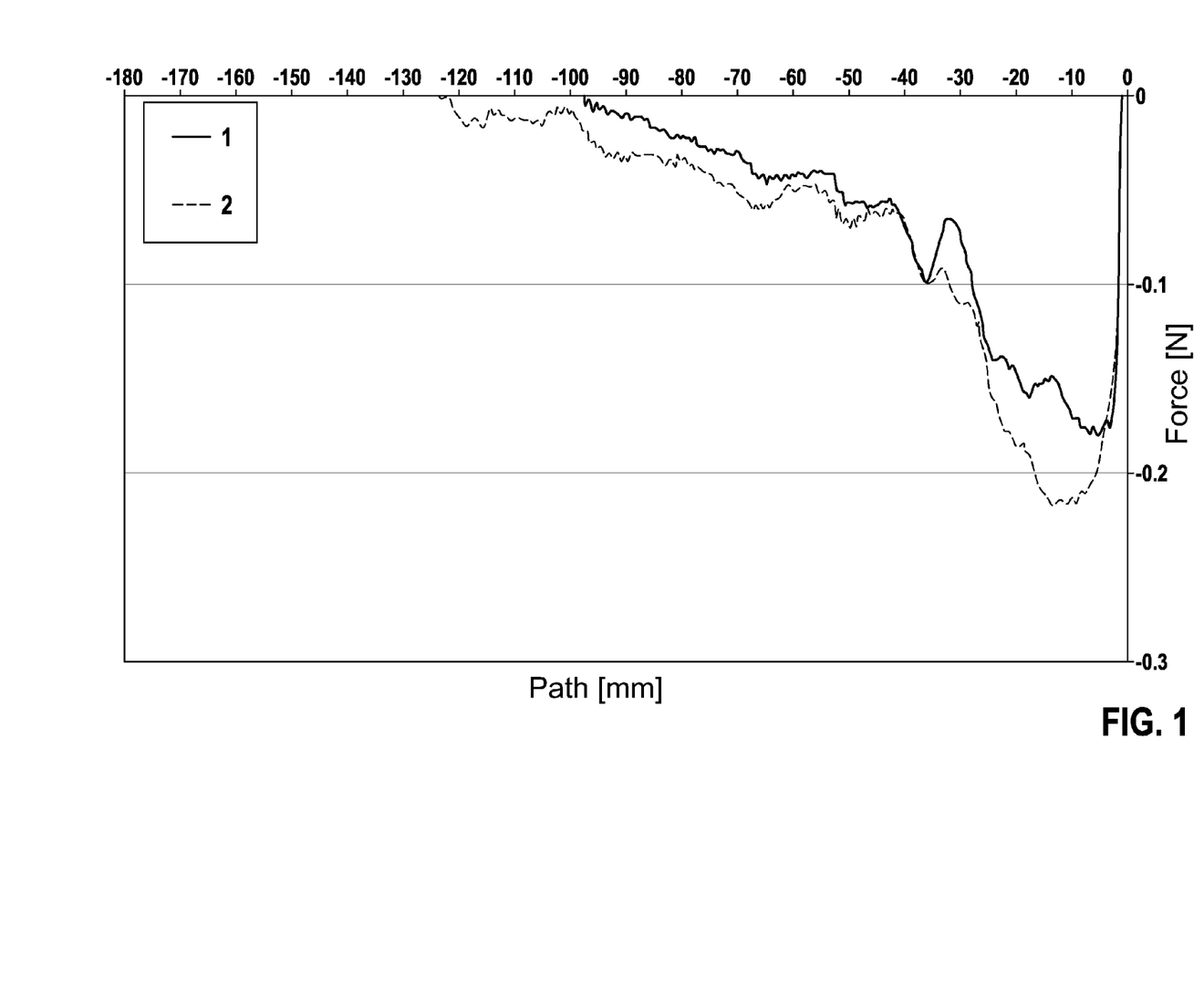
FIG. 1: Wire friction experiment in a track tester (Interventional Device Testing Equipment from Machine Solutions Inc. (MSI)) in water having a temperature of 37° C.
  Guide wire used: Galeo M 0.014"; guide wire model from BIOTRONIK
  1) inside shaft having inner layer according to the invention
  2) inside shaft containing 100% HDPE as the inner layer

FIG. 1 shows the results of a wire friction experiment (so-called pull back experiment) in the comparison between a tube according to the invention comprising an inner layer according to the invention (and thus comprising a solid body according to the invention) and a comparison tube having the same design, in which the inner layer was made 100% of semi-crystalline HDPE (Purell® GD6250).

Figure 6:
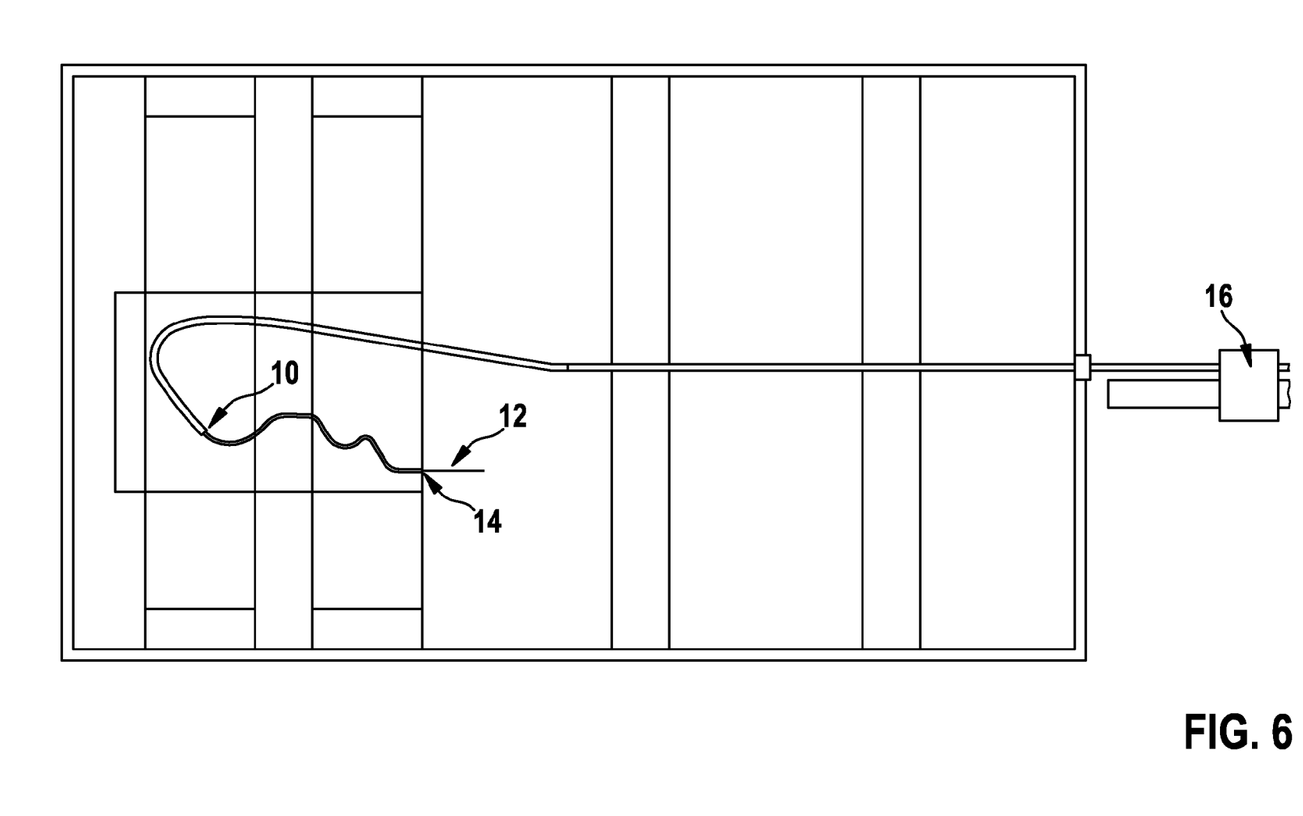
FIG. 6: Schematic design of the model for the wire friction experiment in the track tester from MSI at 37° C.
  10) tip of guide catheter
  12) distal end of guide wire
  14) end of tube to be tested
  16) proximal end of the guide wire, fastened to the stepper motor and force measuring unit of the track tester from MSI

The measurement of the results shown in FIG. 1 was carried out as follows: An inner tube is placed in a model (according to BIOTRONIK's test instruction 105112), and a guide wire (Galeo M) is introduced in the lumen. The proximal force is measured when the guide wire is pulled out of the inner tube in a track bath from MSI in water controlled to a temperature of 37±2° C. A schematic test set-up is shown in FIG. 6.

The result is as follows: The energy that is required to move the guide wire in the inside shaft comprising the material composition according to the invention in the inner layer, the shaft being introduced in a coronary model, is reduced by 23% as compared to an inside shaft comprising an inner layer not according to the invention made of 100% semi-crystalline HDPE. The reduction of the maximum force, or friction force, is reduced by 17% for the inside shaft comprising an inner layer made of the material composition according to the invention.

EXAMPLE 2

Trackability of Balloon-expandable Stent Delivery Catheters Comprising Inside Shafts, the Inner Layers of which Consist of the Material Composition According to the Invention The trackability, which is to say the force necessary to push a catheter on the guide wire through an anatomic model of a coronary artery, was determined based on balloon-expandable stent delivery catheters having an inside shaft comprising an inner layer consisting of the material composition according to the invention, in comparison with catheters having the same design except for the inner layer of the internal shaft, in which the inner layer is made 100% of semi-crystalline HDPE.

For determining trackability and pushability (Example 3), balloon-expandable stent delivery catheters comprising a stent having a nominal diameter of 3.0 mm and a length of 15 mm were produced, in accordance with the ProKinetic Energy Catheter Design from BIOTRONIK, from the inside tube according to the invention from Example 1 and the reference tube from Example 1, as well as from a further inside tube comprising an inner layer made of PTFE. The differing inside shafts used in the catheters correspond to the inside shafts of Example 1. The guide wire used for measuring trackability (Example 2) and pushability (Example 3) in a temperature-controlled water bath of 37±2° C. of the track tester from MSI also corresponds to that of Example 1.

Figure 2:
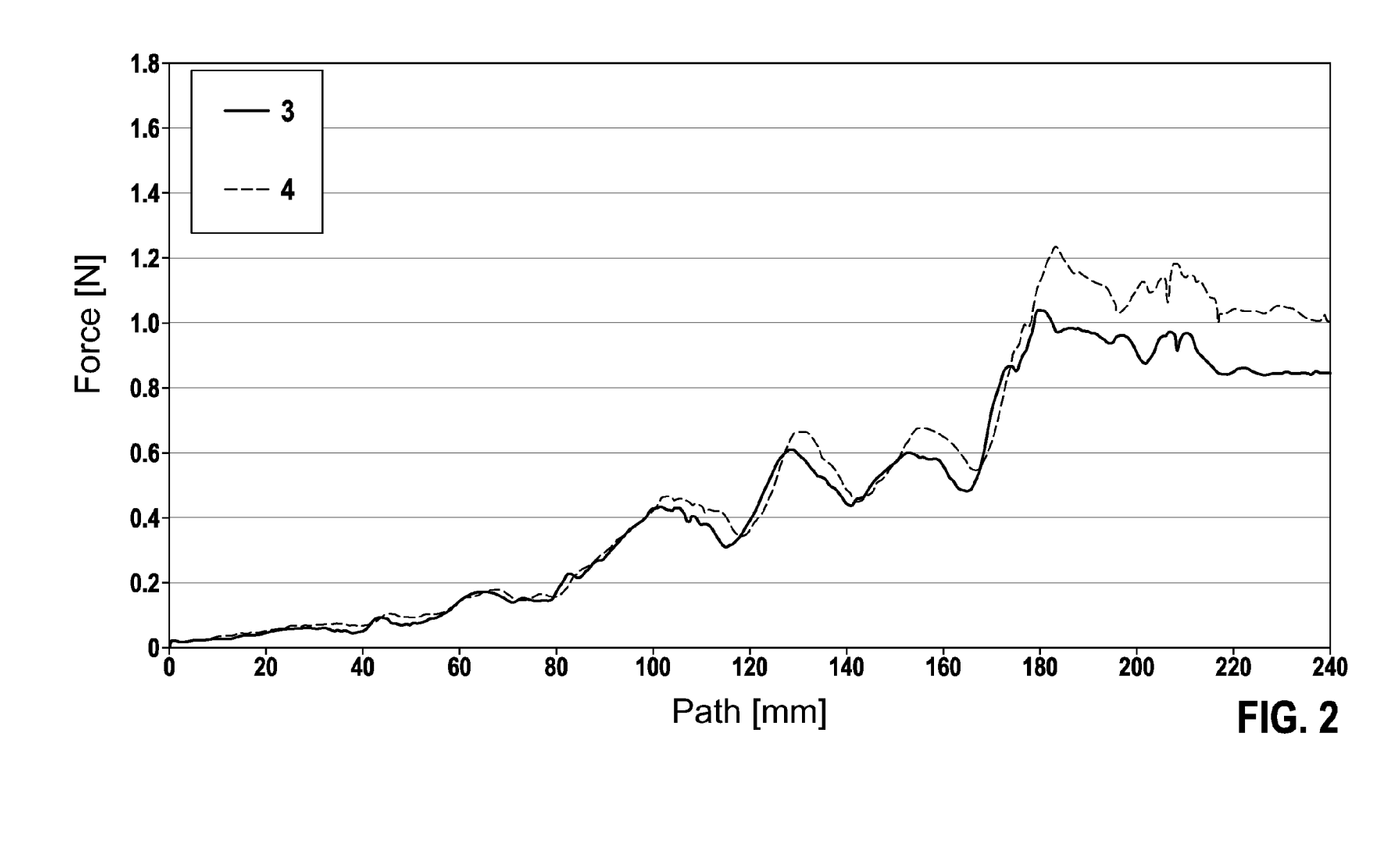
FIG. 2: Trackability in an aorta model with a Teflon® tube as the friction partner in a track tester [see above] from MSI in water having a temperature of 37° C.
  Guide wire used: Galeo M "014; guide catheter: Cordis Vista 5F JL 4LBT
  3) stent release catheter comprising an inside shaft having an inner layer according to the invention
  4) stent release catheter comprising an inside shaft having an inner layer made of 100% HDPE

FIG. 2 shows the results of a trackability experiment in an aorta model using Teflon as the friction partner, wherein a layer system according to the invention was compared to one not according to the invention.

The experiment was carried out as follows: A guide wire is pushed through an anatomical model, which is described in K.-P. Schmitz et al.; "Biomol. Technik" 48 (2003) Supplement pp. 66-67. The model is temperature-controlled in 37±2° C. water. The catheter is introduced in the model on the guide wire through a guide catheter, which is Vista 5F JL5LBT from Cordis. The catheter is then advanced in the model on the guide wire (Galeo M, from BIOTRONIK) and the force necessary to do so is measured proximally in the track tester from MSI. The model is identical to the model described in FIG. 1, Schmitz et al (see above).

The following result was obtained: The maximum force, this being the friction force, for pushing the catheters through the model is lower with the catheter comprising the material composition according to the invention in the inner layer of the inside shaft by 16% to 27% as compared to the reference catheter.

Figure 3:
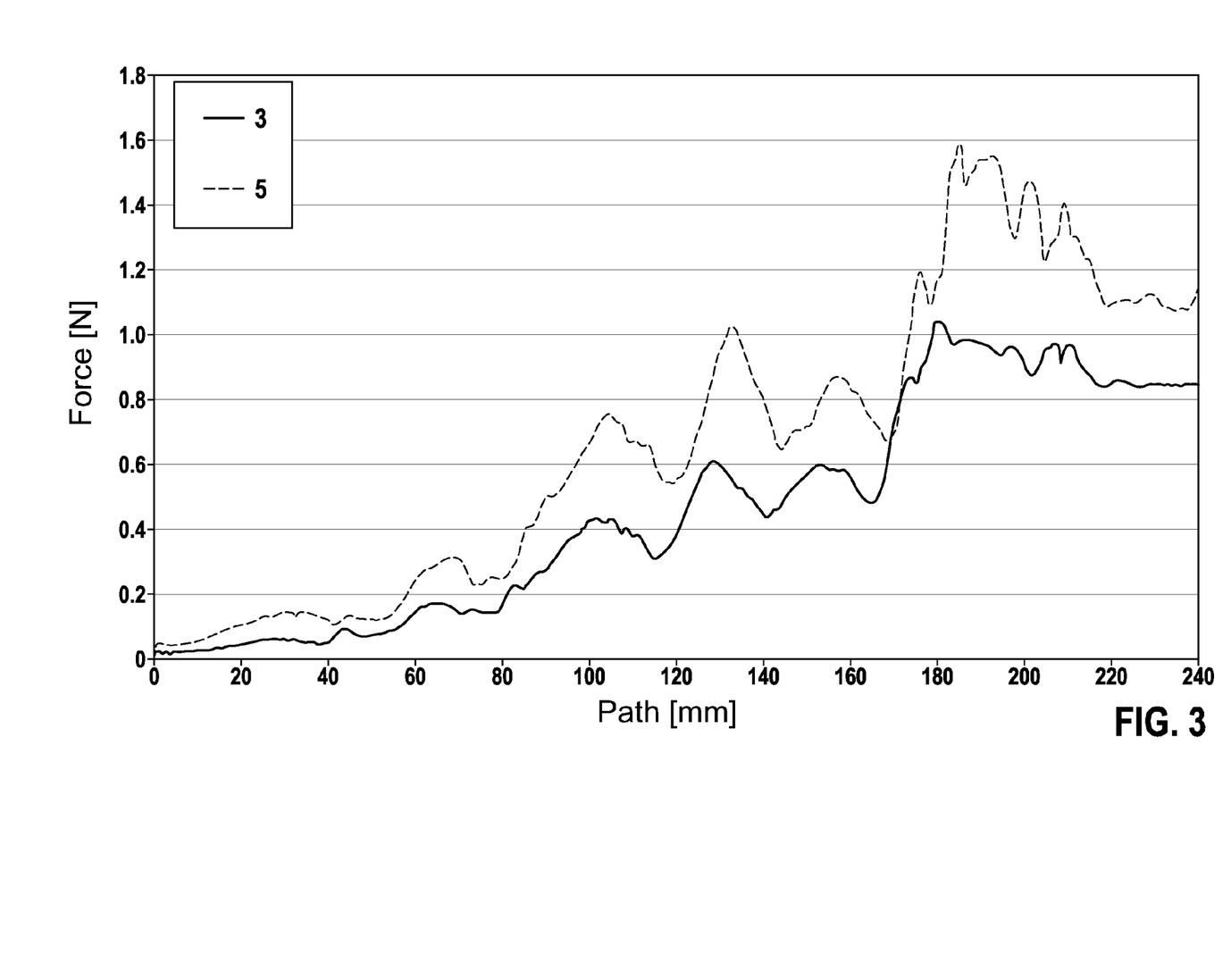
FIG. 3: Trackability in an aorta model with a Teflon® tube as the friction partner in a track tester (see above) from MSI in water having a temperature of 37° C.
  Guide wire used: Galeo M "014; guide catheter: Cordis Vista 5F JL 4LBT
  3) stent release catheter comprising an inside shaft having an inner layer according to the invention
  5) stent release catheter comprising an inside shaft having a Teflon layer as the inner layer

In a further trackability experiment (analogous design and analogous execution), catheters comprising an inside shaft having an inner layer consisting of the material composition according to the invention (as before) was compared to balloon-expandable, nearly identical catheters comprising an inside shaft having a PTFE inner layer (as before), however in a slightly longer usable length. In this case, the catheter comprising the material composition according to the invention in the inner layer of the inside shaft showed a reduction in the maximum required force, the friction force, of 26 to 34%.

FIG. 3 shows the results of the second trackability test.

EXAMPLE 3

Push Test (Pushability) of Balloon-expandable Stent Delivery Catheters Comprising Inside Shafts, the Inner Layers of which Consist of the Material Composition According to the invention Compared to the two reference catheters, the two aforementioned balloon-expandable catheters comprising an inner layer of the inside shaft consisting of the material composition according to the invention showed higher force transmission from the proximal ends to the distal ends of the catheters.

Pushability of a catheter system describes the ability to transmit a force that is applied proximally to the catheter to the distal end of the catheter.

Figure 7:
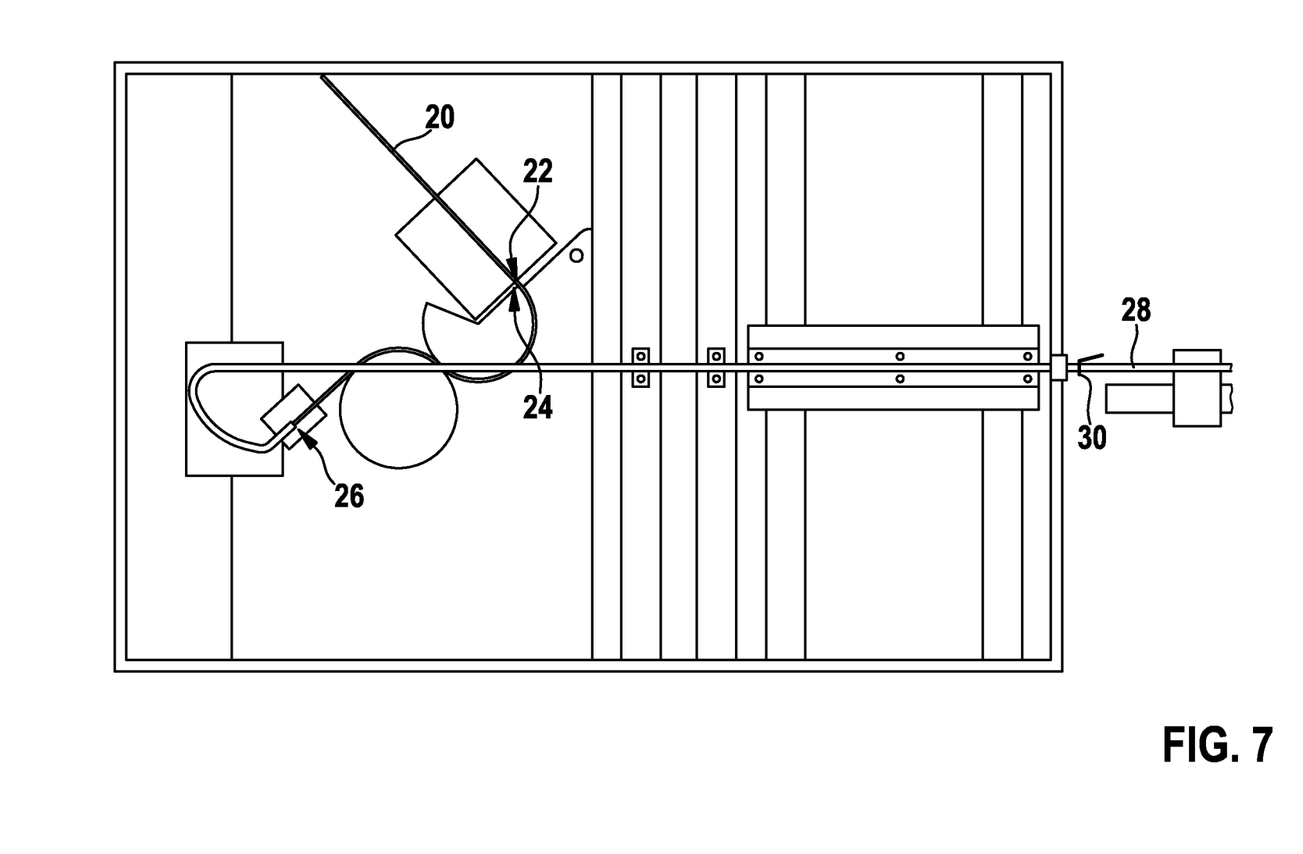
FIG. 7: Schematic design of the model for the push test in the track tester from MSI at 37° C.
  20) distal tip of the guide wire
  22) starting point of the measurement
  24) recording of the distal force
  26) distal end of guide catheter
  28) proximal end of the catheter, fastened to the stepper motor and force measuring unit of the track tester from MSI
  30) proximal fixation of the guide wire

The measurements were carried out as follows: A catheter is pushed on a guide wire (Galeo M, from Biotronik) through a model (according to BIOTRONIK's test instruction 105113) in the track tester from MSI in temperature controlled water of 37±2° C. A load cell is fastened at the distal end. By applying differing forces at the proximal end of the catheter, the resulting distal force is determined. A schematic set-up of the model is shown in FIG. 7.

The catheters used correspond to the catheters of Example 2 (FIGS. 2 and 3).

Figure 4:
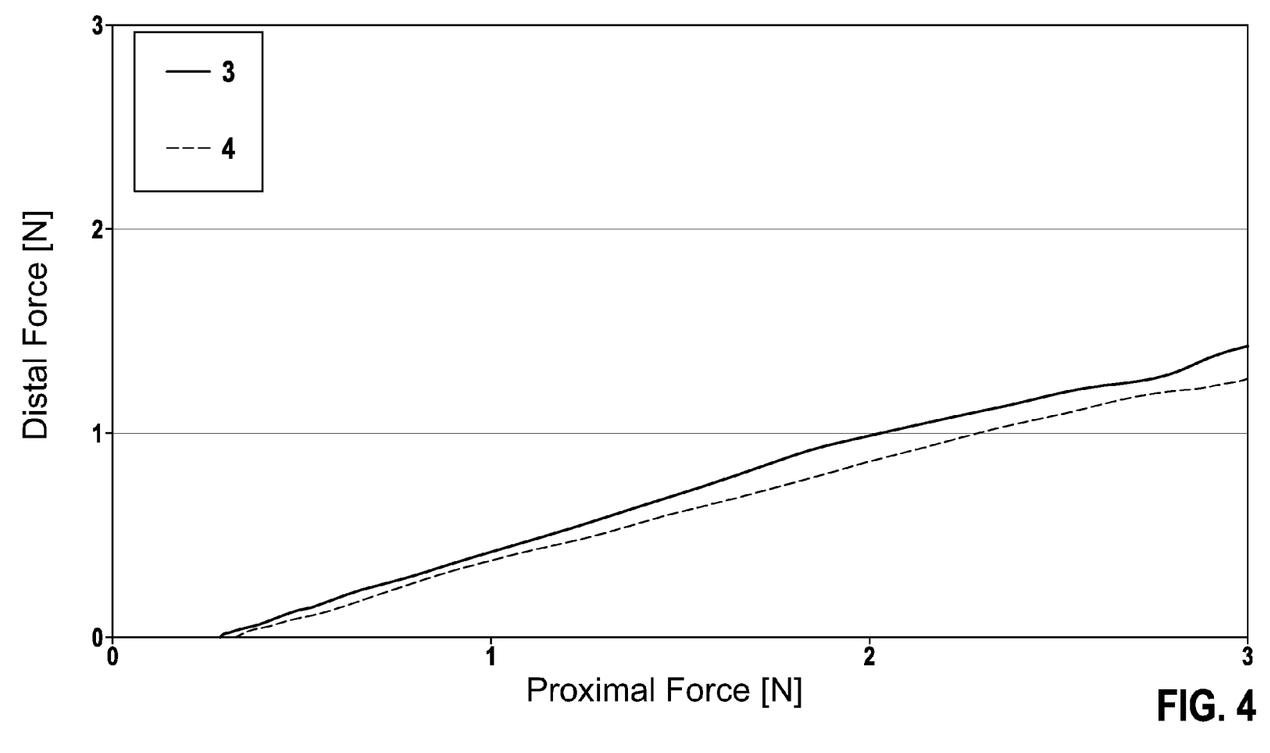
FIG. 4: Push test in a track tester (see above) from MSI in water having a temperature of 37° C.
  3) stent release catheter comprising an inside shaft having an inner layer according to the invention
  4) stent release catheter comprising an inside shaft having an inner layer made of 100% HDPE

FIG. 4 shows the results of the push test using the tube pair subjected to the first trackability test.

Figure 5:
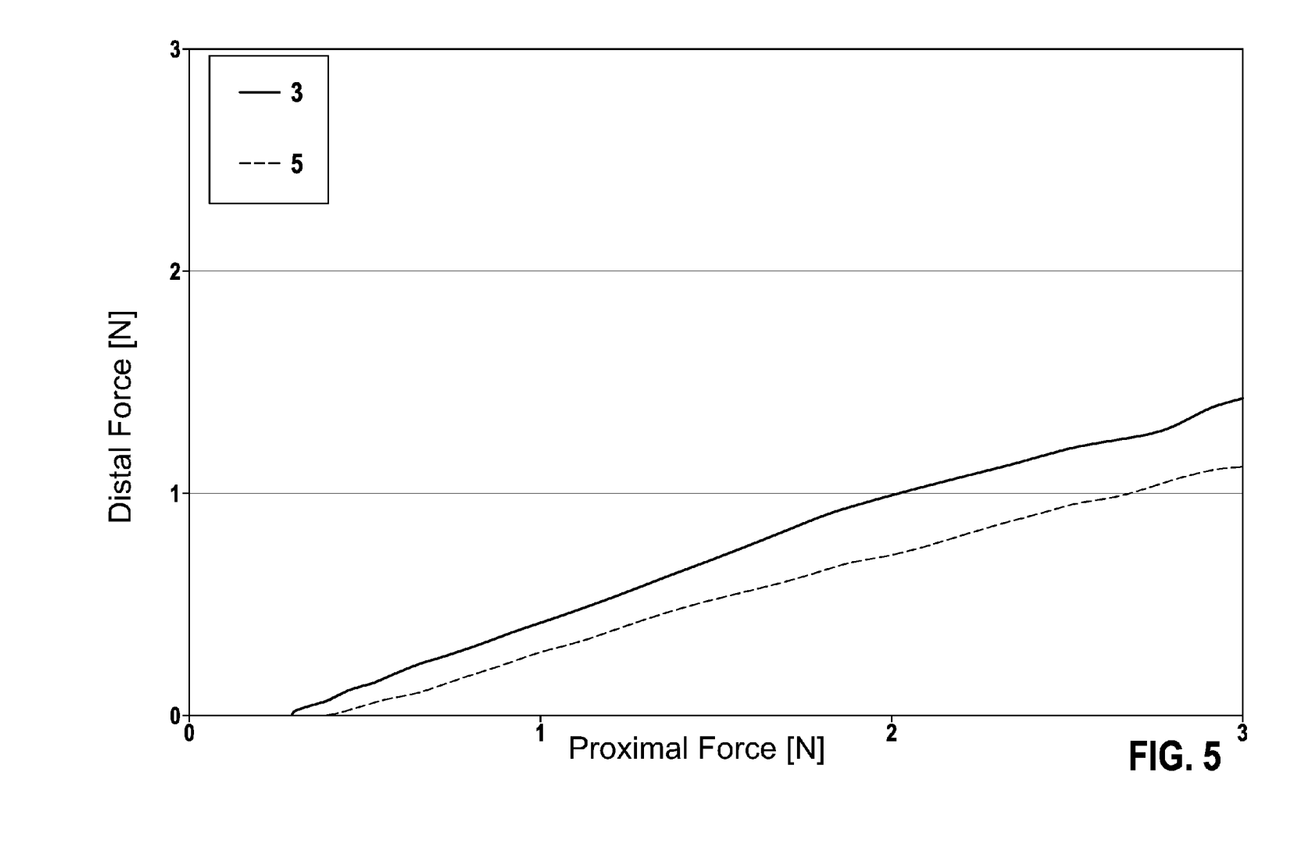
FIG. 5: Push test in a track tester (see above) from MSI in water having a temperature of 37° C.
  3) stent release catheter comprising an inside shaft having an inner layer according to the invention
  5) stent release catheter comprising an inside shaft having a Teflon layer as the inner layer

FIG. 5 shows the results of the push test using the tube pair subjected to the second trackability test (see above).

The result is thus that, for both tube pairs, in each case the tube according to the invention achieves a higher force transmission from the proximal end to the distal end of the catheter as compared to the tube not according to the invention, because of the inside coating according to the invention, for all force inputs that are introduced in which an effect was achieved.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

What is claimed is:

1. A mixture comprising 60-98% by weight polyethylene (PE) and 40-2% by weight cyclic olefin copolymer (COC), wherein ≥70% by weight relative to the total mass of PE in the mixture is high density polyethylene (HDPE).

2. The mixture according to claim 1, wherein ≥90% by weight relative to the total mass of PE in the mixture is HDPE.

3. The mixture according to claim 1, wherein the weight percentage relationship between the total mass of PE and the total mass of COC in the mixture is 75-95% by weight to 25-5% by weight, relative to the total mass of PE and COC in the mixture.

4. The mixture according to claim 1, wherein the PE has a melting temperature of 124° C. to 135° C. and/or a density of 0.934 g/ml to 0.966 g/ml and/or a melt flow index (MFI) of 0.3 g/10 min to 5 g/10 min, and the COC has a glass transition temperature (Tg) of 130° C. to 160° C. and a melt volume rate (MVR) of 10 ml/10 min to 20 ml/10 min and/or a refractive index of 1.52 to 1.54.

5. A solid body, optionally an extrusion product or an injection-molded product, consisting of a mixture according to claim 1.

6. The solid body according to claim 5, wherein the mixture consists of PE and COC.

7. A solid body, comprising a mixture made of PE and COC, wherein ≥70% by weight, relative to a total mass of PE, of PE in the mixture is high density polyethylene (HDPE), and/or comprising the solid body according to claim 5, wherein the solid body is selected from the group consisting of a single-layer or multi-layer medical balloon tube, a charging tube for a delivery system, an outside shaft for an RX or over-the-wire catheter, an inner layer or outer layer of coextruded multi-layer tubes, an inside shaft of a catheter, an outside shaft of a catheter, a protector for a catheter, a guide catheter, an insertion system for electrodes, and a release tube for a stent.

8. The solid body according to claim 7, wherein the solid body is part of a stent application device or of a balloon dilation catheter.

9. A method for producing a medical object, comprising the following steps:
providing the mixture according to claim 1; and
jointly extruding the mixture.

10. A method for reducing the friction of an object with respect to metal, comprising the following steps:
providing the mixture according to claim 1; and
coating the object at least partially in a region in which friction with metal can occur with the mixture.

11. A medical tube formed from the mixture according to claim 1, wherein the mixture comprises 90% HDPE and 10% COC.

* * * * *